(12) United States Patent
Brink et al.

(10) Patent No.: US 8,188,062 B2
(45) Date of Patent: May 29, 2012

(54) DELIVERY OF DNA OR RNA VIA GAP JUNCTIONS FROM HOST CELLS TO TARGET CELLS AND A CELL-BASED DELIVERY SYSTEM FOR ANTISENSE OR SIRNA

(75) Inventors: Peter R. Brink, Setauket, NY (US); Michael R. Rosen, New York, NY (US); Richard B. Robinson, Cresskill, NJ (US); Ira S. Cohen, Stony Brook, NY (US); Arthur Grollman, Setauket, NY (US)

(73) Assignees: The Trustees of Columbia University in the City of New York, New York, NY (US); The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/910,346

(22) Filed: Oct. 22, 2010

(65) Prior Publication Data
US 2011/0076773 A1 Mar. 31, 2011
US 2011/0275156 A2 Nov. 10, 2011

Related U.S. Application Data

(62) Division of application No. 10/583,369, filed as application No. PCT/US2004/042504 on May 24, 2007, now Pat. No. 7,842,673.

(60) Provisional application No. 60/530,555, filed on Dec. 17, 2003.

(51) Int. Cl.
*A01N 43/04* (2006.01)
*A61K 31/70* (2006.01)
*C12Q 1/68* (2006.01)
*C12P 19/34* (2006.01)

(52) U.S. Cl. ............. 514/44; 435/6; 435/91.1; 435/325; 435/375

(58) Field of Classification Search .................... 514/44; 536/24.5
See application file for complete search history.

(56) References Cited

U.S. PATENT DOCUMENTS
5,762,926 A 6/1998 Gage et al.

OTHER PUBLICATIONS

Valiunas et al. (J. Physiol 568.2:459-468, 2005).*
Burt et al. (American Journal of Physiology: Cell Physiology, 2001 vol. 280:C500-C508).*
Hammond et al. (Nature Reviews, 2001 vol. 2:110-119).*
Brink et al. (Biochimica et Biophysica Acta, 2001, Article in Press, Available online Oct. 2, 2011, pp. 1-6).*
Agrawal et al., "Antisense therapeutics: is it as simple as complementary base recognition", "Molecular Medicine Today", Feb. 2000, pp. 72-81, vol. 6, Publisher: Elsevier Science Ltd.

(Continued)

*Primary Examiner* — Terra Cotta Gibbs
(74) *Attorney, Agent, or Firm* — Evans & Molinelli PLLC; Judith A. Evans

(57) ABSTRACT

A method of delivering an oligonucleotide or a plasmid expressing an oligonucleotide into a target cell comprises introducing an oligonucleotide into a donor cell, particularly a stem cell, and contacting the target cell with the donor cell under conditions permitting the donor cell to form a gap junction with the target cell, whereby the oligonucleotide or a product of the oligonucleotide is delivered into the target cell from the donor cell.

22 Claims, 2 Drawing Sheets

OTHER PUBLICATIONS

Braasch et al, "Novel Antisense and Petide Nucleic Acid Strategies for Controlling Gene Expression", "Biochemistry", Apr. 9, 2002, pp. 4503-4510, vol. 41, No. 14, Publisher: American Chemical Society.

Burt et al. , "Alteration of Cx43:Cx40 expression ratio in A7r5 cells", "American Journal of Physiology: Cell PhysiologyAmerican Journal of Physiology: Cell Physiology", 2001, pp. C500-C508, vol. 280.

Elbashir et al, "Duplexes of 21-nucleotide RNAs mediate RNA interference in cultured mammalian cells", "Nature", May 24, 2001, pp. 494-498, vol. 411, Publisher: Macmillan Magazines Ltd., Published in: www.nature.com.

EPO, "Supplementary European Search Report", Jun. 22, 2007, Publisher: European Patent Office, pp. 1-4, Published in: The Hague.

Frendo et al., "Involvement of connexin 43 in human trophoblast cell fusion and differentiation", "Journal of Cell Science", 2003, pp. 3413-3421, vol. 116, No. 16.

Gewirtz et al. , "Facilitating Oligonucleotide Delivery: Helping Antisense Deliver on its Promise", "Proc. Natl. Acad. Sci.", Apr. 1996, pp. 3161-3163, vol. 93, Published in: USA.

Giampuzzi et al. , "Down-regulation of Lysyl Oxidase-induced Tumorigenic Transformation in NRK-49F Cells Characterized by Constitutive Activ", "Journal of Biological Chemistry", Aug. 3, 2001, pp. 29226-29232, vol. 276, No. 31, Publisher: American Society for Biochemistry and Molecular Biology, Inc.

Hammond et al. , "Post-Transcriptional Gene Silencing by Double-Stranded RNA", "Nature Reviews", Feb. 2001, pp. 110-119, vol. 2, Publisher: Macmillan Magazines Ltd.

Li et al., "Properties and Regulation of Gap Junctional Hemichannels in the Plasma Membranes of Cultured Cells", "Journal of Cell Biology", Aug. 1, 1996, pp. 1019-1030, vol. 134.

Li et al., "Inhibiting Gap Junctional Intercellular Communication Alters Expression of Differentiation markers in Osteoblastic Cells", "Bone", Dec. 1999, pp. 661-666, vol. 25, No. 6, Publisher: Elsevier.

M. Mesnil et al., "Bystander Killing of Cancer Cells by Herpes Simplex Virus Thymidine Kinase Gene Is Mediated by Connexins", "Proceedings of the National Academy of Sciences of the USA", 1996, pp. 1831-1835, vol. 93, No. 5, Publisher: National Academy of Sciences of the United States of America, Published in: Database Biosis online.

M. Mesnil et al., "Bystander Effect in Herpes Simplex Virus-Thymidine Kinase/Ganciclovir Cancer Gene Therapy", "Cancer Research", Aug. 1, 2000, pp. 3989-3999, vol. 60, No. 15, Publisher: American Association for Cancer Research, Published in: Database Medline.

Peracchia et al., "Is the Voltage Gate of Connexins $CO_2$-sensitivity? Cx45 Channels and inhibition of Calmodulin Expression", "Journal of Membrane Biology", 2003, pp. 53-62, vol. 195, Publisher: Springer-Verlag.

J. D. Pitts et al., "Permeability of Junctions Between Animal Cells: Intercellular Transfer of Nucleotides but Not of Macromolecules", "Experimental Cell Research", 1977, pp. 153-163, vol. 104, Publisher: Academic Press Inc. (Elsevier), Published in: Amsterdam, NL.

Reed et al, "Molecular Cloning and Functional Expression of human Connexin37, and Endothelial Cell Gap junction Protein", "Journal of Clinical Investigation", Mar. 1993, pp. 997-1004, vol. 91, Publisher: The American Society for Clinical Investigation, Inc.

Rosenthal et al. , "Model systems for the study of the role of PADPRP in essential biological processes", "Biochimie", 1995, pp. 439-443, vol. 77, Publisher: Elsevier, Paris.

Salomon et al. , "Topography of mammalian connexins in human skin", "Journal of Investigational Dermatology", Aug. 1994, p. 1 page, vol. 103, No. 2.

Valiunas et al., "Gap junction channels formed by coexpressed connexin40 and connexin43", "Am. J. physiol. Heart Circ. Physiol.", 2001, pp. H1675-H1689, vol. 281, Publisher: the American Phyiological Society.

V. Valiunas et al., "Cardiac Gap Junction Channels Show Quantitative Differences in Selectivity", "Circulation Research", 2002, pp. 104-111, vol. 91, Publisher: American Heart Association, Published in: www.circresaha.org.

Valiunas et al. , "Connexin-specifc cell-to-cell transfer of short interfering RNA by gap junctions", "J. Physiol", 2005, pp. 459-468, vol. 568.2, Publisher: The Physiological Society.

W. Zhu et al., "Increased Genetic Stability of HeLa Cells after Connexin 43 Gene Transfection", "Cancer Research", 1997, pp. 2148-2150, vol. 57, No. 11, Publisher: American Association for Cancer Research, Published in: Database Biosis online.

* cited by examiner

DELIVERY OF DNA OR RNA VIA GAP JUNCTIONS FROM HOST CELLS TO TARGET CELLS AND A CELL-BASED DELIVERY SYSTEM FOR ANTISENSE OR SIRNA

CROSS-REFERENCE TO RELATED APPLICATION

This application is a Divisional Application of application Ser. No. 10/583,369 filed May 24, 2007, and issued as U.S. Pat. No. 7,842,673 which claims benefit of PCT Application No. PCT/US2004/042504 filed May 24, 2007, which claims benefit of, and priority from, U.S. Provisional Application No. 60/530,555, filed Dec. 17, 2003 the entire contents of which are hereby incorporated by reference as if fully set forth herein, under 35 U.S.C. §120.

STATEMENT OF GOVERNMENTAL INTEREST

This invention was made with Government support under Contract No. HL-28958 awarded by the National Heart, Lung, and Blood Institute (NHLBI) of the National Institutes of Health (NIH) and Contract No. GM-55263 awarded by the National Institute of General Medical Sciences (NIGMS) of NIH. The Government has certain rights in the invention.

BACKGROUND OF THE INVENTION

Throughout this application, various publications are referenced within footnotes or in the text within parentheses. These publications in their entireties are hereby incorporated by reference into this application to more fully describe the state of the art to which this invention pertains. Full bibliographic citations for these references may be found at the end of the specification, preceding the claims.

As described in commonly owned prior application U.S. Ser. No. 10/342,506, filed Jan. 15, 2003, and in publications (1,2) incorporated by reference herein, stem cells have been used to form gap junctions with target tissues. Such stem cells can influence the activity of the target tissues by delivering gene products or small molecules. However, nucleotides in the form of antisense RNA, or DNA, have not been delivered by host cells (such as human mesenchymal stem cells (hMSCs)) to target tissues.

SUMMARY OF THE INVENTION

According to the present invention, RNA can be passed through gap junctions so that engineered cells can be used to deliver RNA to target cells.

According to the present invention, oligonucleotides, either single and double stranded, can be passed through gap junctions formed by C x 43 in HELA cell pairs, as demonstrated by a single electrode delivery of fluorescent-tagged oligonucleotides to a donor cell and determining their transfer to the target cell via gap junction mediated communication. Accordingly, the invention provides for delivery of oligonucleotides to target cells using any donor cell that forms gap junctions.

According to the invention, a method of delivering an oligonucleotide or a plasmid expressing an oligonucleotide into a target cell is provided, comprising introducing an oligonucleotide into a donor cell, and contacting the target cell with the donor cell under conditions permitting the donor cell to form a gap junction with the target cell, whereby the oligonucleotide or a product of the oligonucleotide is delivered into the target cell from the donor cell.

According to the present invention, a method of delivering an oligonucleotide into a target cell, is provided, comprising introducing an oligonucleotide into a human mesenchymal stem cell or other donor cell, and contacting the target cell with the human mesenchymal stem cell or other donor cell under conditions permitting the donor cell to form a gap junction with the target cell, whereby the oligonucleotide or its peptide product is delivered into the target cell from the donor cell.

According to the present invention, a method of delivering an oligonucleotide into a syncytial target cell is provided, comprising introducing an oligonucleotide into a donor cell, and contacting the syncytial target cell with the donor cell under conditions permitting the donor cell to form a gap junction with the syncytial target cell, whereby the oligonucleotide is delivered into the syncytial target cell from the donor cell.

According to the present invention, a method of delivering RNA into a target cell is provided, comprising introducing RNA or a plasmid for RNA into a donor cell, and contacting the target cell with the donor cell under conditions permitting the donor cell to form a gap junction with the target cell, whereby the RNA is delivered into the target cell from the donor cell.

According to the present invention, a method of delivering DNA into a target cell is provided, comprising introducing DNA or a plasmid encoding for DNA into a donor cell, and contacting the target cell with the donor cell under conditions permitting the donor cell to form a gap junction with the target cell, whereby the DNA is delivered into the target cell from the donor cell.

The invention provides a useful treatment in which down regulation of gene activity is desirable (e.g., cancer).

As compared to prior methods wherein delivery of RNA or antisense to target cells is done by a naked plasmid, in the present invention the delivery is via cells, and the transfection rate should be much higher.

DESCRIPTION OF THE INVENTION

Figure 1:
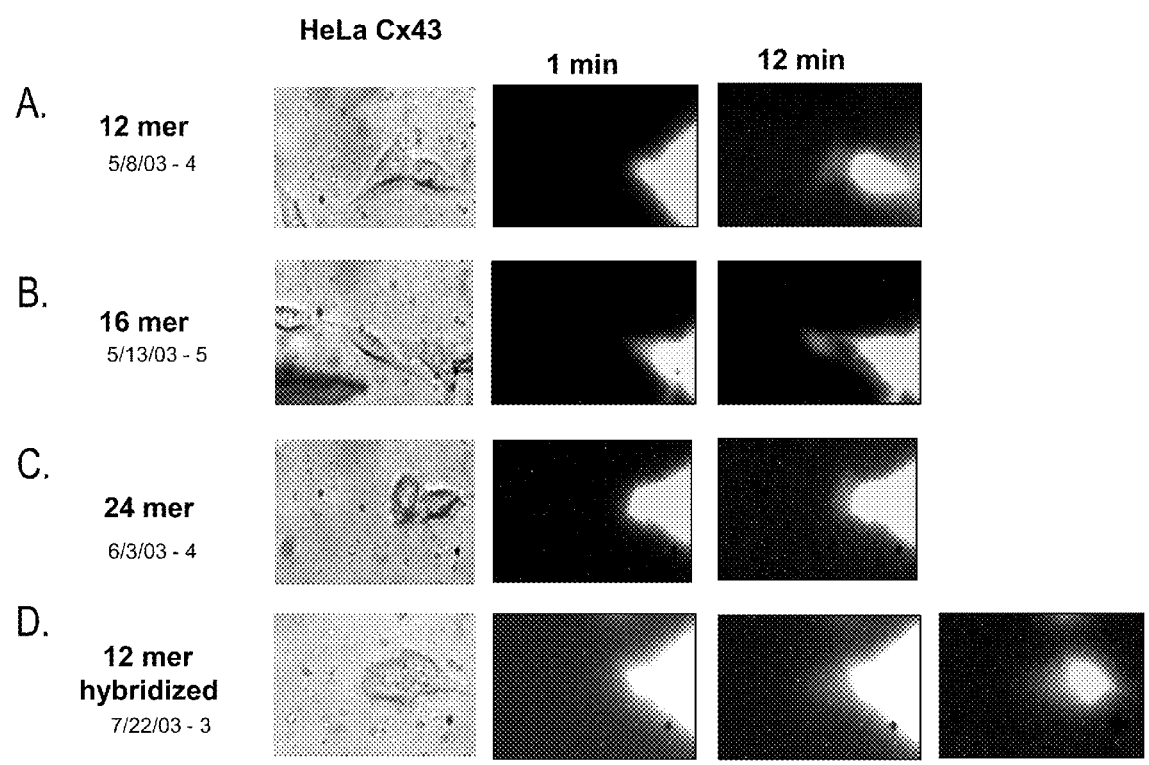
FIG. 1a shows a 12 member single stranded oligonucleotide passing through gap junction channels composed of connexin 43.
FIG. 1b shows a 16 member single stranded oligonucleotide passing through gap junction channels composed of connexin 43.
FIG. 1c shows a 24 member single stranded oligonucleotide passing through gap junction channels composed of connexin 43.
FIG. 1d shows a 24 member double stranded oligonucleotide passing through gap junction channels composed of connexin 43.

According to the invention, a method of delivering an oligonucleotide or a plasmid expressing an oligonucleotide into a target cell is provided, comprising introducing an oligonucleotide into a donor cell, and contacting the target cell with the donor cell under conditions permitting the donor cell to form a gap junction with the target cell, whereby the oligonucleotide or a product of the oligonucleotide is delivered into the target cell from the donor cell.

The oligonucleotide may be RNA that can traverse the gap junction or be transcribed into a peptide that can traverse the gap junction. The oligonucleotide may be DNA. The oligonucleotide may be an antisense oligonucleotide or a cDNA that produces an antisense oligonucleotide that can traverse the gap junction. The oligonucleotide may be a siRNA oligonucleotide or a cDNA that produces a siRNA oligonucleotide that can traverse the gap junction. The oligonucleotide may be a DNA or RNA that produces a peptide that can traverse the gap junction. The plasmid may encode siRNA. The oligonucleotide may comprise 12-24 members. The donor cell may be a human mesenchymal stem cell. The donor cell may be a cell containing or engineered to contain connexin proteins. The target cell may be a cell comprising a syncytial tissue, which may be a cardiac myocyte, a smooth muscle cell, an epithelial cell, a connective tissue cell, or a syncytial cancer cell. The target call may be a white blood cell.

The gap junction channels may be composed of one or more of connexin 43, connexin 40, connexin 45, connexin 32 and connexin 37.

According to the present invention, a method of delivering an oligonucleotide into a target cell is provided, comprising introducing an oligonucleotide into a human mesenchymal stem cell or other donor cell, and contacting the target cell with the human mesenchymal stem cell or other donor cell under conditions permitting the donor cell to form a gap junction with the target cell, whereby the oligonucleotide or its peptide product is delivered into the target cell from the donor cell.

According to the present invention, a method of delivering an oligonucleotide into a syncytial target cell is provided, comprising introducing an oligonucleotide into a donor cell, and contacting the syncytial target cell with the donor cell under conditions permitting the donor cell to form a gap junction with the syncytial target cell, whereby the oligonucleotide is delivered into the syncytial target cell from the donor cell.

According to the present invention, a method of delivering RNA into a target cell is provided, comprising introducing RNA or a plasmid for RNA into a donor cell, and contacting the target cell with the donor cell under conditions permitting the donor cell to form a gap junction with the target cell, whereby the RNA is delivered into the target cell from the donor cell.

According to the present invention, a method of delivering DNA into a target cell is provided, comprising introducing DNA or a plasmid encoding for DNA into a donor cell, and contacting the target cell with the donor cell under conditions permitting the donor cell to form a gap junction with the target cell, whereby the DNA is delivered into the target cell from the donor cell.

The present invention provides a way to pass oligonucleotides (DNA and/or RNA fragments) through gap junction channels. This has been demonstrated in experiments where gap junction channels composed of connexin43 (Cx43) were used in a HeLa cell line.

The experiments determined that oligocomplexes such as DNA or RNA sequences of defined length are able to pass through a gap junction channel. DNA or RNA forms alpha helixes in solution with minor diameters of 0.9-1.0 nm. Oligonucleotides in the 12-24 member size range are of particular interest. Unique sequences of DNA which could not be broken down into smaller fragments were tagged with a fluorescent probe from Morpholino, a company which specializes in the manufacture of oligo sequences.

The experiments were conducted with a 12 member oligonucleotide, a 16 member oligonucleotide and a 24 member oligonucleotide. The results demonstrated that all three single stranded forms pass through gap junction channels composed of Cx43 (FIGS. 1a, b, and c). Further, two 12 member compliments were hybridized producing a double stranded form and its passage was measured (FIG. 1d). The double stranded version has only a small increase in its minor diameter.

Figure 2:
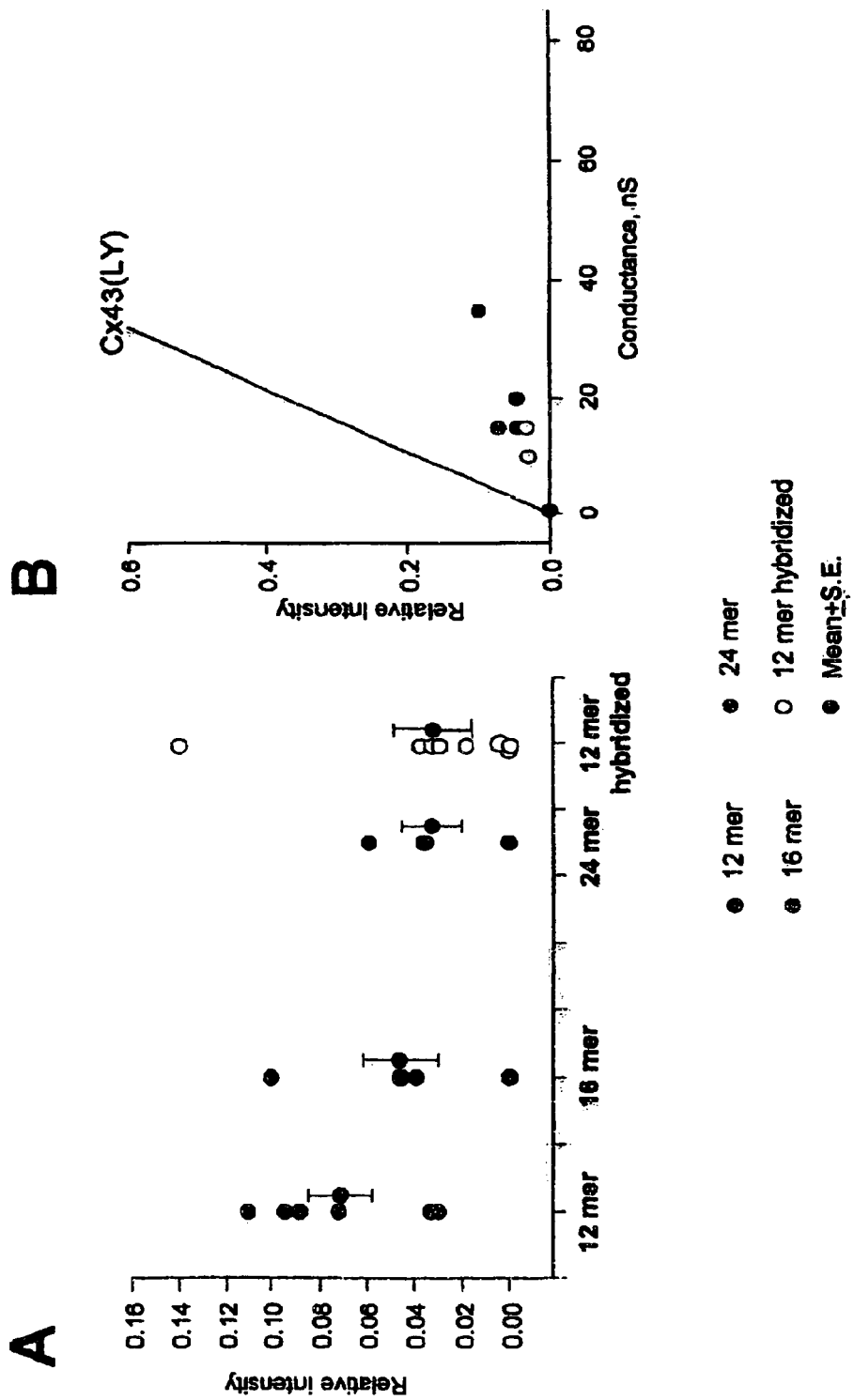
FIG. 2a shows a summary of the data where the x-axis is the length of the oligonucleotide, and the y-axis is the relative intensity of the fluorescent tag in the recipient cell (the cell on the left in all of the examples of FIG. 1) 12 minutes after delivery of the oligonucleotide to the source cell.
FIG. 2b is a graphic representation of junctional conductance on the x-axis versus relative intensity of the fluorescent tag on the y-axis.

FIG. 2A shows a summary of the data where the X-axis is the length of the oligonucleotide. The hybridized 12 member oligonucleotide is plotted out of sequence on the X-axis. The Y-axis is the relative intensity of the fluorescent tag in the recipient cell (the cell on the left in all of the examples of FIG. 1) 12 minutes after delivery of the oligonucleotide to the source cell. For each oligonucleotide the individual experimentally derived values are shown along with the mean and standard deviation for each oligonucleotide. In a number of experiments junctional conductance and the transfer of fluorescently labeled oligonucleotide were monitored simultaneously.

FIG. 2B is a graphic representation of junctional conductance on the X-axis versus relative intensity of the fluorescent tag on the Y-axis. For comparison the conductance-intensity relationship for Lucifer Yellow passage through Cx43 gap junction channels is shown (Valiunas et al., 2002) (2). In all cases the relative intensity, which represents the transfer rate from one cell to another, is 5-10 times less than the Lucifer Yellow fluorescence intensity in recipient cells. This lower transfer rate is consistent with the rod-like dimensions of the oligonucleotide, whose minor diameter is 1.0 nm, being less mobile in solution than Lucifer Yellow.

These observations demonstrate that gap junction channels are a feasible delivery port for molecules such as silencing RNA (siRNA) or any other molecule of similar dimension.

We have previously demonstrated that hMSCs make gap junctions with each other and target cells. We have also demonstrated previously that one can load plasmids into stem cells by electroporation. The present results demonstrate that any donor cell type which forms gap junctions with another target cell type (this includes hMSCs as potential donor or target cells) can be used as a vehicle to deliver RNA or DNA.

REFERENCES

1. Plotnikov A N, Shlapakova I N, Danilo P Jr, Herron A, Potapova I, Lu Z, Valiunas V, Doronin S, Brink P R, Robinson R B, Cohen I S, Rosen M R: Human mesenchymal stem cells transfected with HCN2 as a gene delivery system to induce pacemaker function in canine heart. Circulation 108: IV-547, 2003.
2. Valiunas et al., 2002 Cardiac gap junction channels show quantitative differences in selectivity. Cir. Res. 91:104-111

We claim:
1. A method of delivering an oligonucleotide into a target cell comprising:
   a) introducing the oligonucleotide or a plasmid expressing the oligonucleotide into a donor cell; and
   b) contacting the target cell with the donor cell under conditions permitting the donor cell to form a gap junction channel composed of connexin 40 with the target cell, whereby the oligonucleotide is delivered into the target cell from the donor cell by traversing the gap junction and wherein the oligonucleotide is 12-24 nucleotides in length.

2. The method of claim 1, wherein the oligonucleotide is RNA that can traverse the gap junction.

3. The method of claim 1, wherein the oligonucleotide is DNA.

4. The method of claim 1, wherein the oligonucleotide is an antisense oligonucleotide.

5. The method of claim 1, wherein the oligonucleotide is an siRNA.

6. The method of claim 1, wherein the oligonucleotide is a DNA or RNA.

7. The method of claim 1, wherein the plasmid encodes siRNA.

8. The method of claim 1, wherein the oligonucleotide is 18-22 nucleotides in length.

9. The method of claim 1, wherein the donor cell is a human mesenchymal stem cell.

10. The method of claim 1, wherein the donor cell is a cell containing, or engineered to contain connexin 40.

11. The method of claim 1, wherein the target cell is present in a syncytial tissue.

12. The method of claim 11, wherein the cell in the syncytial tissue is selected from the group consisting of a cardiac myocyte, a smooth muscle cell, an epithelial cell, a connective tissue cell, and a syncytial cancer cell.

13. The method of claim 1, wherein the target call is a white blood cell.

14. The method of claim 1, wherein the gap junction channel further comprises a second connexin selected from the group consisting of connexin 43 connexin 45, and connexin 37.

15. A method of delivering an oligonucleotide into a target cell comprising:
   a) introducing the oligonucleotide into a human mesenchymal stem cell or other donor cell; and
   b) contacting the target cell with the human mesenchymal stem cell or other donor cell under conditions permitting the donor cell to form a gap junction channel composed of connexin 40 with the target cell, whereby the oligonucleotide is delivered into the target cell from the donor cell by traversing the gap junction and wherein the oligonucleotide is 12-24 nucleotides in length.

16. A method of delivering an oligonucleotide into a syncytial target cell comprising:
   a) introducing the oligonucleotide into a donor cell in vitro; and
   b) contacting the syncytial target cell with the donor cell under conditions permitting the donor cell to form a gap junction channel with the syncytial target cell, whereby the oligonucleotide is delivered into the syncytial target cell from the donor cell by traversing the gap junction wherein the gap junction is composed of connexin 40 and wherein the oligonucleotide is 12-24 nucleotides in length.

17. A method of delivering RNA into a target cell comprising:
   a) introducing RNA or a plasmid transcribable into RNA into a donor cell in vitro; and
   b) contacting the target cell with the donor cell under conditions "permitting the donor cell to form a gap junction channel composed of connexin 40 with the target cell", whereby the RNA is delivered into the target cell from the donor cell by traversing the gap junction and wherein the RNA is 12-24 nucleotides in length.

18. A method of delivering DNA into a target cell comprising:
   a) introducing a DNA or a plasmid coding for the DNA into a donor cell in vitro; and
   b) contacting the target cell with the donor cell under conditions "permitting the donor cell to form a gap junction channel composed of connexin 40 with the target cell", whereby the DNA is delivered into the target cell from the donor cell by traversing the gap junction and wherein the DNA is 12-24 nucleotides in length.

19. The method of claim 15, wherein the donor cell is a human mesenchymal stem cell.

20. The method of claim 16, wherein the donor cell is a human mesenchymal stem cell.

21. The method of claim 17, wherein the donor cell is a human mesenchymal stem cell.

22. The method of claim 18, wherein the donor cell is a human mesenchymal stem cell.

* * * * *